United States Patent [19]

Brooks

[11] 4,078,077
[45] Mar. 7, 1978

[54] CYCLODIENE INSECTICIDES

[75] Inventor: Gerald Thomas Brooks, Burgess Hill, England

[73] Assignee: National Research Development Corporation, London, England

[21] Appl. No.: 739,324

[22] Filed: Nov. 5, 1976

[30] Foreign Application Priority Data

Nov. 6, 1975 United Kingdom ............... 46076/75

[51] Int. Cl.$^2$ ...................... A01N 9/28; C07D 307/87
[52] U.S. Cl. ............................... 424/285; 260/346.71; 260/348.53; 424/278
[58] Field of Search ................. 260/346.2 M; 424/285

[56] References Cited

U.S. PATENT DOCUMENTS

| | | | |
|---|---|---|---|
| 2,655,513 | 10/1953 | Kleinman | 260/346.2 M |
| 2,655,514 | 10/1953 | Kleinman | 260/346.2 M |
| 3,305,563 | 2/1967 | Mark | 260/346.2 M |

Primary Examiner—Henry R. Jiles
Assistant Examiner—Bernard Dentz
Attorney, Agent, or Firm—Jacobs & Jacobs

[57] ABSTRACT

Analogues and derivatives of dieldrin and dihydroaldrin containing a reduced number of chlorine atoms, and hence improved biodegradability, have the formula

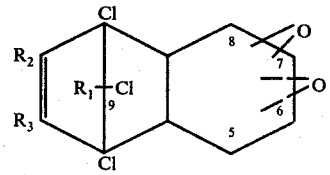

wherein $R_1$, $R_2$, and $R_3$ and H or Cl at least one of them being H, and the oxygen bridge is 5:8, 6:7, or 7:8, or both 5:8 and 6:7.

12 Claims, No Drawings

CYCLODIENE INSECTICIDES

This invention relates to insecticides and more particularly to cyclodiene insecticides.

Among the class of cyclodiene insecticides Dieldrin has achieved prominence and has been used for many years. However the high chlorine content and hence poor biodegradability of this compound are factors which makes its use increasingly questionable.

It has now been found that certain compounds related to Dieldrin have comparable levels of toxicity towards insects but are especially attractive on account of their reduced chlorine content.

The present invention comprises compounds of structural formula

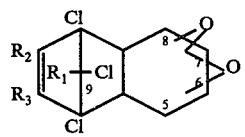

Wherein $R_1 R_2 R_3$ are H or cl, at least one of them being H, and the oxygen bridge is 5:98, 6:7, or 7:8 or both 5:8 and 6:7.

These compounds are toxic to tsetse fly, stable fly, housefly, and blowfly and are biodegradable.

The compounds of the present invention can be prepared from certain analogues and isomers of dieldrin and dihaloaldrin as specified hereinafter. The starting materials are subjected to reactions which result in successive replacement of vinylic chlorine atoms by hydrogen, followed by replacement of chlorine at the 9-carbon atom. The latter step results in a mixture of 9-syn-and 9-anti-dechloro isomers which can be separated by fractional crystallisation or chromatographically. The 9-anti-dechloro isomers are relatively inactive. Alternatively the chlorine atoms may be replaced in the reverse order.

Replacement of vinylic chlorines can be achieved by photodechlorination under the influence of ultraviolet light. Replacement of chlorine at dichloromethano bridge can be achieved by reduction with certain hydrides e.g. tri-n-butyl tin hydride in presence of a free radical initiator or with a mixture of sodium borohydride and a cobaltous salt.

The compounds of the present invention may be produced from the following starting materials:

1. The 5,8-oxa-analogue of 6,7-dihydroaldrin (ODA)
2. The 6,7-oxa-isomer of ODA
3. The 7,8-oxa-isomer of ODA, and
4. The 5,8-oxa-analogue of dieldrin (oxadieldrin)

In a further alternative method, the starting material can be a corresponding bis-2,3-dechloroderivative which can be converted into the desired 9-syn-dechloroderivative in one stage.

The compounds of this invention can be used with synergists, e.g. sesamex or piperonyl butoxide.

The invention is illustrated in the following Examples:

EXAMPLE 1

Oxadieldrin (0.25 millimols) is treated under reflux in benzene (0.5 ml) with tri-n-butyl tin hydride (80 microliters) in presence of α-α' azobis-isobutyronitrile (0.5mg) for 1-2 hrs. Conversion of the reactant is monitored by thin layer chromatography on aluminium oxide plates, with hexane/ether (3:1). The resulting mixture of 9-syn and 9-anti-dechloro isomers is precipitated with an equal volume of light petroleum ether (40° – 60°) and separated by recrystallisation from methanol or by TLC or column chromatography on alkaline alumina using ether/light petroleum ether as eluant. Thus the required 9-syn-dechloro isomer (SOD) is separated from the 9-anti isomer which remains on the column.

The 9-syn dechloro isomer is dissolved in hexane and irradiated for five hours in a silica spectrophotometer cell (1 or 2 cm path) using a Camag Universal UV lamp type TL-900 (254 nm).

The desired product is 2,9-syn-bisdechloro-oxadieldrin.

2. To produce 2, 3, 9-syn-trisdechloro-oxadieldrin, Example (1) is repeated except that the irradiation step is conducted with a more powerful source of radiation, a Hanovia U.V.5 500 medium pressure arc.

3. Alternatively, irradiation of oxadieldrin with, successively, the Camag and Hanovia U.V. sources gives 2,3-bisdechlorooxadieldrin.

EXAMPLE 2

Oxadieldrin (0.08 millimols; 30 mg.) is irradiated in methanol (8 ml) for four hours in a silica spectrophotometer cell (2cm path) using the Camag Universal UV lamp type TL-900 (254 nm). Following evaporation of methanol, the residue is dissolved in acetone/60°–80° light petroleum (1:4) and chromatographed on alkaline alumina (grade IV) with 60°–80° light petroleum as eluting solvent. The product, 2-monodechloro-oxadieldrin (20 mg) has m.p. 173°–174°.

EXAMPLE 3

2-monodechloro-oxadieldrin (0.06 millimols) is irradiated in methanol (8 ml) with the Hanovia U.V.S. 500 medium pressure arc and its conversion monitored by thin layer chromatography and gas-liquid chromatography. After 1-2 hours the solvent is evaporated and the product purified by chromatography on alumina as in the previous Example. The product 2,3 - bisdechloro-oxadieldrin has m.p. 221°.

EXAMPLE 4

Oxadihydroaldrin (0.5 millimols) is treated under reflux in benzene (1 ml) with tri-n-butyl tin hydride (0.5 millimols; 160 microliters) in presence of α,α'-azobis-isobutyronitrile (1 mg) for 1-2 hrs. Following precipitation of the mixture of 9-syn-dechloro- and 9-anti-dechloro- isomers with an equal volume of light petroleum ether (40°-60°), the predominant less polar syn-dechloro isomer is extracted from the solid with small amounts of ether and further purified by chromatography on alkaline alumina (grade III) using ether/light petroleum ether (1:9) as eluant. The product has m.p. 139°–141°.

EXAMPLE 5

Oxadihydroaldrin (0.08 millimols) is irradiated in hexane (8 ml) for 1-2 hours in a silica spectrophotometer cell (2 cm path) using the Camag Universal lamp type TL-900 (254 nm). The crude product obtained by evaporating the solvent is chromatographed on alkaline alumina (grade IV) with 40°-60° light petroleum as eluant to give 2-monodechloro-oxadihydroaldrin (50%) m.p. 113°–115°.

EXAMPLE 6

The 7,8-oxa-isomer of 6,7-dihydroaldrin 0.1 millimols is irradiated for 2 hrs. in hexane (8 ml) in a silica spectrophotometer cell (2 cm path) with the Camag Universal UV lamp type TL-900 (254 nm), to give a mixture of the 2- and 3-monodechloroderivatives. These products are separated by thin layer chromatography on plates of neutral alumina (0.5 mm) using ether/hexane (1:9) as developing solvent, to give a solid, m.p. 90°–92° and a liquid.

By proceeding as described above the following typical compounds shown in the Table are obtained. The compounds are tabulated under code name, structure, and physical constants, then by chemical name or description. Toxicity to blowflies for representative compounds are also given.

TABLE

|  | $R_1$ | $R_2$ | $R_3$ | O> | m.p.° C |
|---|---|---|---|---|---|
| MOD | Cl | H | Cl | 6:7,5:8 | 173–174 |
| SOD | H | Cl | Cl | 6:7,5:8 | 239 |
| BOD | Cl | H | H | 6:7,5:8 | 221 |
| MODA | Cl | H | Cl | 5:8 | 113–115 |
| SODA | H | Cl | Cl | 5:8 | 139–141 |
| MSODA | H | H | Cl | 5:8 | 95–98 |
| MHCE | Cl | H | Cl | 7:8 | 90–92/ |
| (mixture) | Cl | Cl | H | 7:8 | liquid |
| SHCE | H | Cl | Cl | 7:8 | 83–84 |
| BHCE | Cl | H | H | 7:8 | 99–100 |

CHEMICAL NAMES

| | |
|---|---|
| MOD | 2-mono dechloro oxadieldrin |
| SOD | 9-syn dechloro oxadieldrin |
| BOD | 2,3-bis dechloro oxadieldrin |
| MODA | 2-monodechloro oxadihydro aldrin |
| SODA | 9-syn-dechloro oxadihydro aldrin |
| MSODA | 2,9-syn-bisdechloro-oxadihydro aldrin |
| MHCE | a mixture of the 2- and 3- mono dechloro derivatives of the 7,8 oxa isomers of oxadihydroaldrin |
| SHCE | The 9-syn-dechloro derivative of the 7,8 isomer of oxadihydroaldrin |
| BHCE | The 2,3-bis-dechloro derivative of the 7,8 isomer of oxadihydroaldrin |

TOXICITY TABLE

| | (LD50 (± SE) per microgram) |
|---|---|
| MOD | 0.079 ± 0.0043 |
| SOD | 0.060 ± 0.0056 |
| BOD | 0.112 ± 0.013 |
| MODA | 2.88 ± 0.186 (0.062 synergised) |
| SODA | 1.32 ± 0.272 |
| MHCE | 15.0 (3.3 synergised) |
| SHCE | 8.4 (1.8 synergised) |

I claim:

1. A compound of the class represented by the formulas:

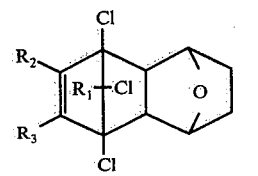

and

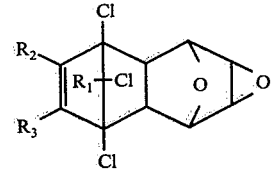

wherein each of $R_1$, $R_2$ and $R_3$ is hydrogen or chloro, at least one being hydrogen and wherein $R_1$ is syn with respect to the double bond.

2. A compound according to claim 1 having the formula:

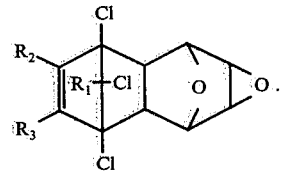

3. The compound according to claim 2 wherein $R_1$ and $R_3$ are chloro and $R_2$ is hydrogen.

4. The compound according to claim 2 wherein $R_1$ is hydrogen and $R_2$ and $R_3$ are chloro.

5. The compound according to claim 2 wherein $R_1$ is chloro and $R_2$ and $R_3$ are hydrogen.

6. A compound according to claim 1 having the formula:

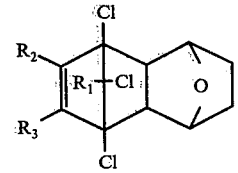

7. The compound according to claim 6 wherein $R_1$ and $R_3$ are chloro and $R_2$ is hydrogen.

8. The compound according to claim 6 wherein $R_1$ is hydrogen and $R_2$ and $R_3$ are chloro.

9. The compound according to claim 6 wherein $R_1$ and $R_2$ are hydrogen and $R_3$ is chloro.

10. An insecticidal composition comprising an insecticidally effective amount of a compound according to claim 1 and a carrier.

11. The composition according to claim 10 including an insecticidal synergist selected from the group consisting of sesamex or piperonyl butoxide.

12. The method of achieving an insecticidal effect which comprises applying to insects an insecticidally effective amount of a compound according to claim 1.

* * * * *